United States Patent [19]

DuBois et al.

[11] 4,283,434
[45] Aug. 11, 1981

[54] SULFAMO DIHYDROCHALCONE SWEETENERS

[76] Inventors: Grant E. DuBois, 4256 Ruthelma Ave., Palo Alto, Calif. 94306; Rebecca A. G. Stephenson, 636 Maple St., Redwood City, Calif. 94063

[21] Appl. No.: 140,064

[22] Filed: Apr. 14, 1980

[51] Int. Cl.$^3$ ............................................. A23L 1/236
[52] U.S. Cl. ................................... 426/548; 426/804; 564/354
[58] Field of Search ................ 426/548, 804; 564/354; 424/357

[56] References Cited

U.S. PATENT DOCUMENTS

| | | | |
|---|---|---|---|
| 3,751,270 | 8/1973 | Rizzi | 426/548 |
| 3,828,030 | 8/1974 | Kinugasa et al. | 564/354 X |
| 3,855,301 | 12/1974 | Rizzi | 568/314 |
| 3,956,375 | 5/1976 | Farkas et al. | 562/464 |
| 3,974,299 | 8/1976 | Crosby et al. | 426/548 |
| 3,976,790 | 8/1976 | Crosby et al. | 426/548 X |
| 4,055,678 | 10/1977 | Crosby et al. | 426/548 |
| 4,226,804 | 10/1980 | DuBois et al. | 426/548 X |

Primary Examiner—Esther M. Kepplinger
Attorney, Agent, or Firm—William H. Benz

[57] ABSTRACT

Sulfamo dihydrochalcones of the formula

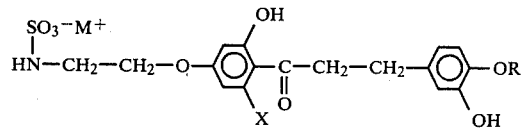

are disclosed wherein M+ is a physiologically acceptable cation, X is H or OH, and R is a lower alkyl. These materials are useful as sweeteners for edibles. They may be prepared by sulfonating the corresponding amino dihydrochalcone using, for example, catechol sulfate.

13 Claims, No Drawings

SULFAMO DIHYDROCHALCONE SWEETENERS

BACKGROUND OF THE INVENTION

1. Field of the Invention

This invention concerns synthetic sweeteners. More particularly, it concerns a new group of sulfamo dihydrochalcone compounds, their use as sweeteners for edible compositions such as foodstuffs, and certain amino dihydrochalcone intermediates.

2. Background

Dihydrochalcones are compounds having a

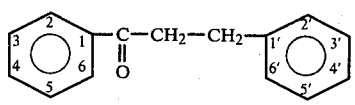

basic structure. A number of such compounds, both natural and synthetic, have been disclosed in the prior art. These materials vary from one another by the nature and placement of substituents on the aromatic rings.

In 1963, dihydrochalcones took on increased importance when it was discovered that some, but by no means all, of their number are sweet (Horowitz and Gentili, U.S. Pat. No. 3,087,871, issued Apr. 30, 1963). The earliest examples of sweet dihydrochalcones were derived from naturally occurring materials (flavanones) having saccharide residues attached at position four. More recently, applicants, their coworkers, and others have disclosed several sweet dihydrochalcones having smaller and simpler substituents at their four position as evidenced by: Rizzi, U.S. Pat. No. 3,855,301, issued Dec. 17, 1974; Rizzi, U.S. Pat. No. 3,751,270, issued Aug. 7, 1973; Farkus et al., U.S. Pat. No. 3,956,375, issued May 11, 1976; Crosby et al., U.S. Pat. No. 3,974,299, issued Aug. 10, 1976; Crosby et al., U.S. Pat. No. 3,976,790, issued Aug. 24, 1976; and Crosby et al., U.S. Pat. No. 4,055,678, issued Oct. 25, 1977, as well as pending United States Patent Application Ser. No. 19,054, now U.S. Pat. No. 4,226,804, which shows dihydrochalcones having an amino acid type structure at their 4 position. This work has repeatedly confirmed the empirical nature of the taste-chemical structure relationship. The exact nature of substituents and their placement on the molecule are critical. A change which is minor on its face may have a major effect on the taste properties of the dihydrochalcone. Two taste-related major goals of dihydrochalcone sweetener research are: (1) To provide compounds having solubility in aqueous media adequate to form suitably sweet consumer products; and (2) To eliminate, or at least minimize, the menthol-like aftertaste and prolonged sweet aftertastes which have plagued many of the dihydrochalcones prepared heretofore. The present invention seeks to realize these goals.

STATEMENT OF THE INVENTION

We have now discovered a group of new dihydrochalcones which have attractive sweetener properties. These materials, which are classifiable as sulfamo dihydrochalcones, are represented structurally as shown in General Formula I

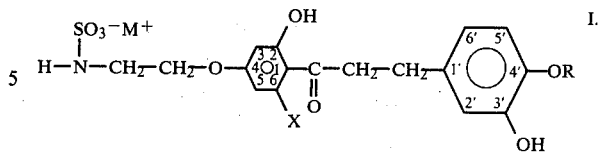

wherein R is a lower alkyl of from 1 to 3 carbons inclusive, X is hydrogen or hydroxy, and M+ is a physiologically acceptable cation. These materials may be named 2, 3′, 6-trihydroxy and 2,3′-dihydroxy-4-(2-sulfamoethoxy)-4′-alkoxydihydrochalcone salts. These materials impart sweet flavors to foods, beverages, medicaments and other comestibles.

DETAILED DESCRIPTION OF THE INVENTION

The Compounds

The compounds of the present invention have the structure shown in General Formula I. In that formula R is an alkyl, more particularly a 1, 2 or 3 carbon alkyl that preferably is linear, i.e., methyl, ethyl or n-propyl. Methyl is the most preferred R.

X is either hydrogen or hydroxy, with hydroxy being preferred. M+ is a physiologically acceptable cation. As used herein, a "physiologically acceptable cation" is defined to include ammonium and the cations of the third and fourth period metals which are nontoxic, i.e., Na(I), K(I), Mg(II), Ca(II), Al(III), Mn(II), and Zn(II). Preferred cations are the cations of the third and fourth period group I and II metals, i.e., Na(I), K(I), Mg(II), and Ca(II), with K being the most preferred metal cation. In the structural formulae of this specification and claims, the divalent calcium cation will be shown as ½ Ca++ to indicate a charge balance with the monovalent sulfo group. Other polyvalent cations will be shown similarly. In actual practice, of course, the Ca++ is associated with two monovalent dihydrochalcone groups. A most preferred compound is that material of Formula I wherein R is —CH₃, M+ is K+ and X is —OH.

Preparation

The materials of General Formula I may be conveniently formed, in a general sense, by sulfonating the amino functionality of the dihydrochalcones shown in General Formula II

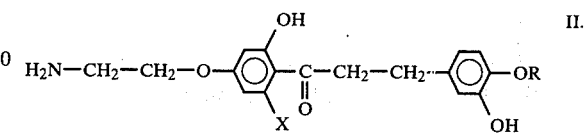

such as with catechol sulfate. The dihydrochalcones of General Formula II are themselves new compounds which may be prepared by substituting the 7 position of the flavanones shown in General Formula III

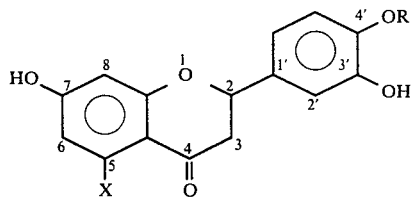

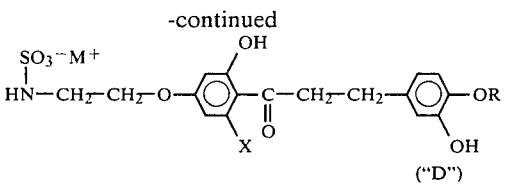

with N-carbobenzyloxy-2-bromoethylamine or an equivalent electrophilic addition agent and thereafter removing the carbobenzyloxy protecting group and opening the flavanone to the desired dihydrochalcone configuration. The flavanones of Formula III include hesperetin and its X equals hydrogen and its R equals $C_2H_5$ and $C_3H_7$ equivalents.

This preparative sceheme may be shown as follows.

Step A

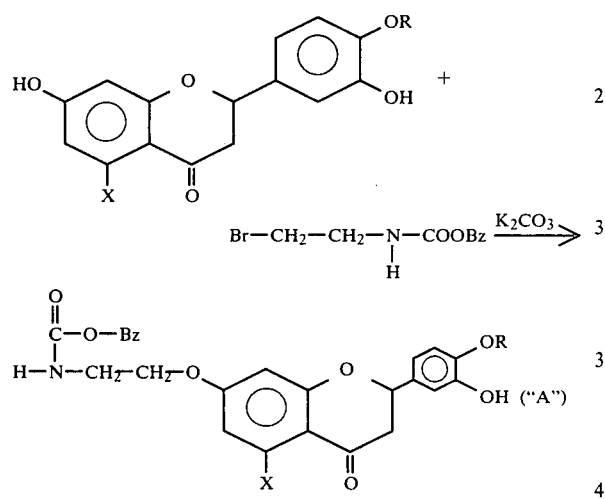

Step B

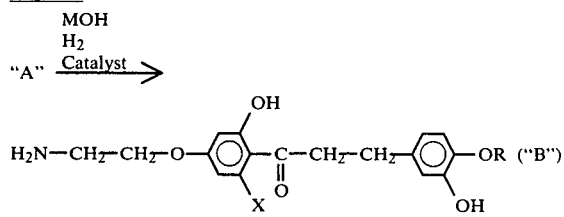

Step C

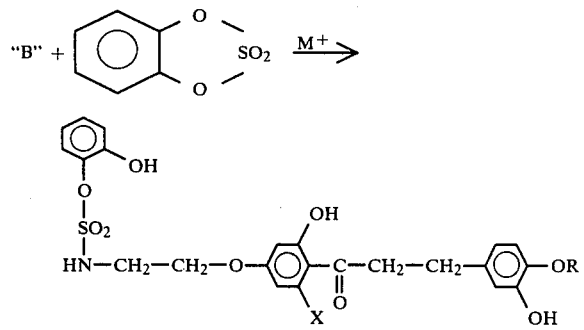

Step D

The addition of the protected amine to the flavanone 7 position (Step A, above) is carried out as follows. N-carbobenzyloxy-2-bromoethylamine or an equivalent protected ethylamine are combined in a liquid phase polar aprotic reaction medium. Suitable media include N,N-dimethylformamide (DMF), dimethylsulfoxide, hexamethylphosphoramide, and the like with DMF generally being preferred. The molar amounts of flavanone and protected amine are about equal with moderate excesses of the protected amine, i.e., 1 to 3, preferably 1 to 2 and most preferably 1 to 1.5 equivalents per mole of flavanone being preferred. The protected amine can be added in stages, if desired.

An acid acceptor, such as an alkali metal carbonate, bicarbonate or hydroxide, and preferably $Na_2CO_3$ or $K_2CO_3$, is present during the alkylation reaction. This material is generally present in a molar amount about equal to the moles of flavanone—i.e., 1–1.5 equivalents, basis flavanone. The reaction is carried out under moderate to elevated temperatures. Generally, somewhat elevated temperatures, such as 35° C. to 100° C. and preferably 45° C. to 80° C. are employed and require relatively long reaction times such as from 10 to 100 hours and preferably 15 to 80 hours to complete. Time, of course, is inversely proportional to temperature. As guidelines, substantial (75%+) reaction occurs at 40° C. in 15–25 hours. At 30° C., 30±% reaction occurs in 24–30 hours. The mixture is generally stirred and blanketed with an inert gas atmosphere. The product of Step A is recovered from the reaction product by conventional workup such as by evaporation of solvent, followed by trituration of the residue with aqueous mineral acid and extraction with ethylacetate, chloroform, or the like, and evaporation to dryness of the organic phase containing the flavanone as an oil.

The opening and hydrogenation of the flavanone to the dihydrochalcone and concomitant removal of the amine protecting group (Step B, above) is carried out in one step with molecular hydrogen base and a suitable catalyst. Mild conditions, such as a gross excess of hydrogen (for example, 10 to 100 psi), dilute aqueous base such as 0.2 to 8 molar, preferably 0.4 to 4 molar alkali metal hydroxide, particularly KOH or NaOH and a noble metal catalyst such as palladium or platinum (preferably palladium), preferably supported such as upon charcoal or the like. Times of from a few hours (such as 3 hours) to about 30 hours, with temperatures of from room temperature (20° C.) to say 35° C. may be employed.

Following hydrogenation and opening, the amine substituted dihydrochalcone product may be recovered, such as by filtration, neutralization, evaporation to dryness and chromatography, such as by liquid chromatography or other equivalent chromatography techniques, or by careful recrystallization.

The sulfonation is generally carried out in two steps, (Steps C and D). Step C may be carried out by contacting the dihydrochalcone product of Step B with catechol sulfate

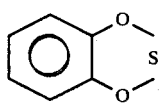

in liquid phase reaction medium at low temperatures in the presence of a weak base. In general, an excess of catechol sulfate (from 1.0 to 2.0 equivalents basis dihydrochalcone) is employed with amounts of 1.0 to 1.5 equivalents being preferred and amounts of 1.0 to 1.25 equivalent being more preferred.

As reaction medium may be employed a halocarbon solvent such as methylene chloride, chloroform, carbon tetrachloride, ethers, ketones or the like. Generally, a polar solvent is preferred with a polar halocarbon solvent such as methylene chloride being most preferred.

The weak base employed is generally an aliphatic amine, especially a tertiary alkyl amine such as trimethyl, triethyl or tripropyl amine or the like. Triethyl amine is preferred. The amine is generally present in a molar amount at least about equal to the amount of catechol sulfate. The amount of weak base plus dihydrochalcone ideally is at least about 2 equivalents (preferably 2-10 equivalents) based on the amount of catechol sulfate.

At low temperatures, such as from −30° C. to +10° C., this addition of catechol sulfate is extremely selective to the amine moiety. Quite desirably, very little side reaction with hydroxyls or other functionalities results. Most preferred temperatures range from −5° C. to 5° C. At these temperatures and preferred temperatures times of from about 1 hour to about 20 hours are employed, with times of from 1 to 5 hours beng preferred.

The catechol sulfate addition product of Step C may be recovered by evaporation of solvent, trituration with aqueous mineral acid and extraction with an organic solvent after which it may be further purified by chromatography, crystallization or the like. The product of Step C is then hydrolyzed in Step D to give the desired sulfamo dihydrochalcone. This hydrolysis may be carried out in liquid phase using about two equivalents of strong base and moderate to elevated temperatures. Water is the preferred reaction medium. Alkali metal or alkaline earth metal hydroxides are preferred bases with NaOH and KOH being more preferred. Generally, 1.5 to 2.5, preferably 1.8 to 2.2, and most preferably about 2 equivalents of base per mole of dihydrochalcone are employed. Temperatures of from about 50° C. to about 120° C. are suitably employed.

The starting flavanones employed in the above synthesis scheme include hesperetin and its X and R substituted equivalents. Hesperetin (X=OH, R=CH$_3$) is available commercially. The other flavanones are less common and generally are prepared. One preparative route for these flavanones involves condensation of an appropriately protected hydroxyacetophenone with an appropriately protected 3-hydroxy-4-alkoxybenzaldehyde in the presence of base to give a chalcone which is then converted to the desired flavanone by treatment with strong acid.

This route may be shown as follows:

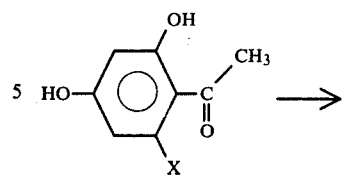

X = H or OH
ACETOPHENONE

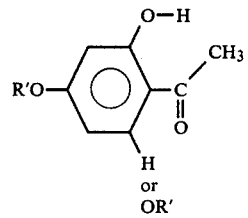

PROTECTED ACETOPHENONE
wherein R' is a protecting group, such as benzyl.

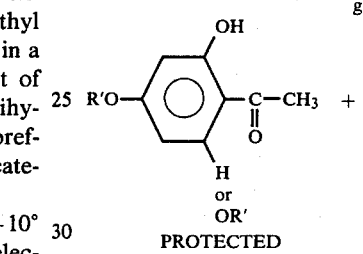

PROTECTED ACETOPHENONE

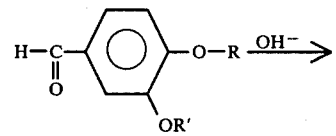

PROTECTED BENZALDEHYDE
wherein R' is a protecting group such as benzyl.

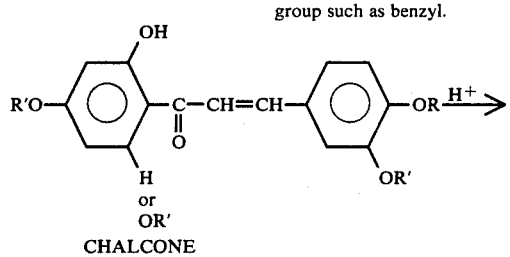

CHALCONE

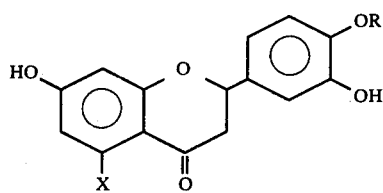

FLAVANONE

These steps can be carried out with process conditions and reagents known to those skilled in the art.

The protected hydroxyacetophenone derivatives, such as 2-hydroxy-4,6-dibenzyloxyacetophenone and 2-hydroxy-4-benzyloxyacetophenone, are prepared from the requisite commercially available hydroxyacetophenones by treatment with a reagent such as a benzyl halide, particularly benzyl bromide or iodide or chloride (1.00-1.25 equivalent based upon the number of hydroxyl groups to be reacted) at 25°-80° C. in polar aprotic liquid phase media. Suitable media include N,N-dimethylformamide (DMF), dimethyl sulfoxide, hexamethylphosphoramide, and the like. An acid acceptor, such as a metal bicarbonate, carbonate, or hydroxide, especially an alkali metal such as $K^+$ of a bicarbonate, carbonate or hydroxide, is also added to the reaction mixture in an amount of from 1.0 to 1.5 equivalents per mole of hydroxyl group being protected. Generally, long reaction times, such as at least 12 hours, are employed with these mild conditions. The most preferred method for preparing the protected hydroxyacetophenones involves the use of benzyl chloride (1.1 equivalent) and $K_2CO_3$ (1.0 equivalent) in DMF at 25°-40° C. Under these conditions the reactions are complete within 3-4 days, with product isolation being carried out by means of a standard aqueous workup.

The protected 4-alkoxy-3-hydroxybenzaldehydes, needed for condensation with the protected hydroxyacetophenones, are prepared by a two-step process from 3,4-dihydroxybenzaldehyde (protocatechualdehyde, commercially available). The first step, which is the preparation of the intermediate 4-alkoxy-3-hydroxybenzaldehydes, involves the treatment of the dihydroxybenzaldehyde with 1.0-1.1 molar equivalents of a 1-3 carbon alkyl halide (especially iodide) in a polar aprotic solvent, such as DMF, at room temperature or slightly above (15°-40° C.). An acid acceptor, such as an alkali metal carbonate, bicarbonate or hydroxide and preferably $K_2CO_3$, in a molar amount about equal to the moles of alkyl halide is required for this reaction. When carried out under these mild conditions, the hydroxyl group at the 4-position, being somewhat more reactive than the hydroxyl group at the 3-position, is alkylated almost exclusively. Protection of the remaining hydroxyl is then effected preferably by benzylation such as at 25°-50° C. with either benzyl chloride or benzyl bromide in DMF or a similar solvent containing 1.0-1.2 molar equivalents of $K_2CO_3$. This completes the preparation of the 4-alkoxy-3-benzyloxybenzaldehydes or their otherwise protected equivalents.

The aldol condensation of the protected hydroxyacetophenones with the 4-alkoxybenzaldehydes, to afford a chalcone, is best carried out with a slight molar excess (preferably 1.1 to 1.5 molar equivalents, basis acetophenone) of benzaldehyde in a lower alkanol (methanol, ethanol, isopropanol) at room temperature to 75° C. A large excess (10-20 molar equivalents) of a strong base, such as NaOH, KOH, NaOEt, or t-BuOK, is needed in order for this reaction to proceed at a reasonable rate. The preferred method for conducting this aldol condensation is to utilize about 1.25 molar equivalents of the benzaldehyde and about 15 molar equivalents of 60% KOH in absolute ethanol (10-15 ml/mmol of acetophenone) at 20°-30° C. Under these conditions, the condensation is complete within 72 hours. The chalcone products may be isolated, after neutralization of the reaction mixture, by a standard aqueous workup. Purification is carried out by recrystallization, with ethanol being the preferred solvent.

The chalcones, when protected as preferred with benzyl groups, undergo debenzylation with concomitant cyclization to the flavanones upon treatment with excess very strong mineral acid. Aqueous HI or HBr (10-20 molar equivalents) in glacial acetic acid (20-60 ml/mmol of chalcone) are preferred acids and are employed at mildly elevated temperatures (30°-100° C.). In general, these reactions proceed rather poorly with other mineral acids, such as HCl, $H_2SO_4$, or $HClO_4$. The final flavanones are isolated, as a mixture with the resulting benzyl halide co-product, by a standard aqueous workup. Purification is best accomplished by chromatographic techniques, such as thin layer chromatography or column chromatography. All of these reactions may be advantageously carried out with stirring and under an inert gas atmosphere.

The dihydrochalcone products of this invention are sweet. They may be used as non-sucrose sweeteners for edibles such as foods, medicaments and beverages. In this use they may be admixed such as by dissolving or dry mixing with the edible as is appropriate. In this use they exhibit a sweetness substantially greater than sucrose and thus should be used in an amount about 1/100-1/1000 that of sucrose. Thus, amounts of from about 0.2 to 0.005% by weight (basis edibles) may be employed.

The present invention will be further shown by the following preparations and examples. These are intended to exemplify the invention and are not to be construed as limiting its scope.

EXAMPLES AND PREPARATIONS

In these Examples and Preparations, the following general conditions apply: All temperatures are in degrees centigrade.

Infrared spectra were recorded on a Perkin Elmer Model 137 spectrophotometer. Proton magnetic resonance spectra were recorded on a Varian Associates T-60A spectrometer (60 MHz) and are recorded in parts per million from tetramethylsilane on the δ scale. Data are reported follows: chemical shift, multiplicity (s=singlet, d=doublet, t=triplet, q=quartet, m=multiplet, br—broad), coupling constant (Hz), integration, and interpretation. Ultraviolet spectra were recorded on a Varian Associates Cary 118 Spectrophotometer. Melting points were determined on a Fisher-Johns melting point apparatus.

High-pressure liquid chromotography (HPLC) was performed on a Waters Associates system equipped with a Model 660 Solvent Programmer, two Model M-6000A pumps and a Schoeffel Instrument Corporation variable wavelength ultraviolet detector and a 30 cm+4 mm C-18 on μ-Bondapak column. Vapor phase chromatography (VPC) was carried out on a Varian Associates Aerograph Model 920 employing a six foot 5% SE-30 on chromosorb G column. Thin layer chromatography (TLC) was carried out on EM Laboratories pre-coated silica gel 60 F-254 plates (5×10 cm).

Diethyl ether, hexane, ethylacetate, chloroform and methylene chloride used were reagent grade solvents from J. T. Baker Chemical Company. Triethylamine was distilled from phosphorous pentoxide and stored over activated molecular sieves 4A. Dimethylformamide (DMF) was distilled from calcium hydride and stored over activated molecular sieves 4A. Pyridine was distilled from barium oxide and stored over activated molecular sieves 4A. Sulfuryl chloride was subjected to simple distillation prior to use.

PREPARATION OF PRECURSORS

Catechol Sulfate

Fifty-five g (0.50 mol) of catechol was dissolved in 79 g of pyridine while stirring vigorously with an overhead stirrer under dry argon in a one-liter three-necked flask equipped with a thermometer and addition funnel. Five hundred ml hexane was then added after which the reaction mixture was cooled to −5° in an ice-salt bath. A solution of 68 g (0.50 mol) of sulfuryl chloride in 100 ml hexane was then added dropwise over 4 hours while carefully maintaining the temperature between −5 and 0°. Stirring at 0° C. was continued overnight after which the reaction mixture was allowed to warm to ambient temperature over 6 hours. The upper layer of the two-layer reaction mixture was decanted after which the lower layer was washed (2×100 ml) with ethyl acetate. The combined washes and upper layer were then washed with 5% $Cu(OAc)_2.H_2O$ until TLC (hexane-ethylacetate; 3:1) indicated the absence of catechol ($R_f$=0.14). The solution was then dried over magnesium sulfate and concentrated yielding 56.7 g of an amber liquid. TLC (hexane-ethylacetate; 3:1) showed one component having $R_f$=0.40. VPC (165° C.; 60 cc/min He flow) showed one major component having RT=5.0 min contaminated by an impurity at 7.5 min. Distillation through a 15 cm vigreux column yielded 45.1 g (52%) of a colorless liquid having bp 76°-8° C. (1.25 mm). Recrystallization from hexane yielded 38.0 g of long, colorless needles having mp 35.5°-36° C. (lit mp 34°-5°).

N-carbobenzyloxy-2-bromoethylamine ("NCBA")

Twenty point five g (0.10 mole) of 2-bromoethylamine hydrobromide was dissolved in 140 ml of water. At 0° C., 15.3 g (0.089 mole) of benzylchloroformate was added, followed by 18.5 g (0.1 moles) of sodium bicarbonate, and the mixture was stirred for 15 minutes at 0°. The mixture was then stirred overnight at room temperature. The mixture was extracted with diethylether (3×250 ml), the combined portions of which were washed thrice with 150 ml portions of saturated sodium bicarbonate, dried with magnesium sulfate and evaporated to yield 20.98 g of the crude N-carbobenzyloxy-2-bromoethylamine (NCBA).

This crude product was combined with similar material from another preparation and purified by chromatography on a silica gel column (400 g J. T. Baker 60-200 mesh). The column was packed and eluted with chloroform to remove residual benzylchloroformate. The desired product was eluted using a (95:5) chloroform-methanol eluent mixture. Fractions were taken. TLC analysis showed the later fractions to be pure N-carbobenzyloxy-2-bromoethylamine (NCBA).

FLAVANONES BY CONDENSING ALDEHYDES AND ACETOPHENONES

A. Preparation of Unprotected Aldehyde Reactants (1) A solution of 2.76 g (20.0 mmoles) of 3,4-dihydroxybenzaldehyde and 2.76 g (20.0 mmoles) of anhydrous potassium carbonate and 3.45 g (22.0 mmoles) of ethyl iodide is prepared in 15 ml of dry DMF and stirred under argon for 24 hours at room temperature. The reaction mixture is poured into 50 ml of water, saturated with sodium chloride and extracted thrice with diethyl ether. The ether extracts are washed with water, and brine, dried and concentrated to yield the ethoxyaldehyde as dark crystals.

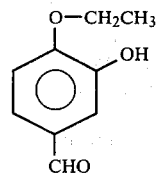

(2) The reaction is repeated using 3.74 g (22.0 mmoles) of n-propyl iodide in place of ethyl iodide to yield the propoxyaldehyde

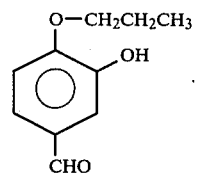

(3) The reaction is repeated using 3.12 g (22.0 mmoles) of methyl iodide in place of ethyl iodide to yield the methoxyaldehyde.

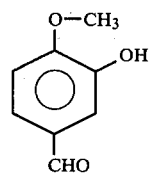

B. Preparation of 4-Alkoxy-3-benzyloxybenzaldehyde

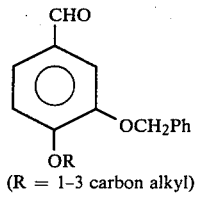

(R = 1-3 carbon alkyl)

4-Alkoxy-3-hydroxybenzaldehyde (1.0 equiv.), benzyl chloride (1.2 equiv.), and $K_2CO_3$ (1.2 equiv.) are stirred in anhydrous DMF at 35° C. for 72 hours. The reaction is poured into ether and the resulting mixture washed thoroughly with $H_2O$, dilute aqueous KOH (until the ethered solution is free of unreacted hydroxybenzaldehyde as determined by TLC), $H_2O$ again, and finally brine. Evaporation affords crude 4-alkoxy-3-benzyloxybenzaldehyde which is generally suitable for use, as is, in the condensation reaction. Additional purification may be achieved by silica gel column chromatography.

C. Preparation of Protected Acetophenones (1) Preparation of 2-Hydroxy-4,6-dibenzyloxyacetophenone

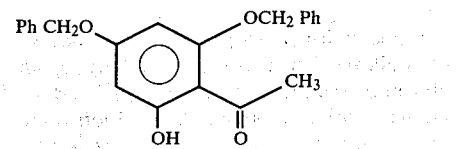

2,4,6-Trihydroxyacetophenone (16.8 g, 0.10 mol, Aldrich Chemical Company) and benzyl chloride (27.8 g, 0.22 mol) were dissolved in 200 ml of dry DMF and the solution was thoroughly purged with argon. The mixture was treated with 27.6 g (0.20 mol) of $K_2CO_3$ and stirred at 35° C. for 84 hours. The reaction was poured into ether (1200 ml) and resulting mixture washed with $H_2O$ (1×500 ml), 5% aqueous KOH solution (3×500 ml), $H_2O$ (1×500 ml), and saturated NaCl solution (1×250 ml). After drying over $MgSO_4$, the ethereal solution was evaporated to afford 27.4 g of crude product as an off-white granular solid. Trituration of the crude product with ether (100 ml), followed by filtration and drying in vacuo provided 13.5 g. (38.8%) of 2-hydroxy-4,6-dibenzyloxyacetophenone as a white solid, mp 101°–102° C., i.e.,

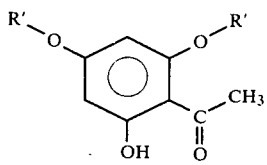

wherein R' is benzyl.

The product was homogeneous by silica gel TLC ($CHCl_3$ elution) and the assigned structure was verified by both NMR and elemental analysis.

(2) Preparation of 2-hydroxy-4-benzyloxyacetophenone

The reaction of (1) above is repeated using 1.1 molar equivalents of benzyl chloride, 1.0 molar equivalent of $K_2CO_3$, and substituting for the above acetophenone 2,4-dihydroxyacetophenone

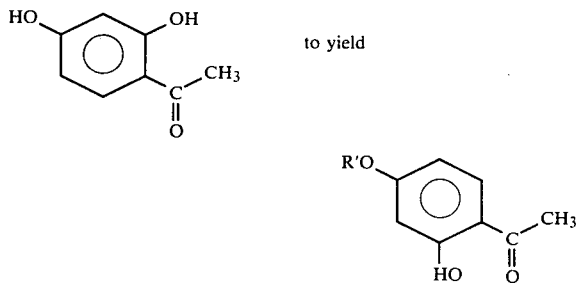

D. Preparation of 2-Hydroxy-3',4,6-tribenzyloxy-4'-alkoxychalcone

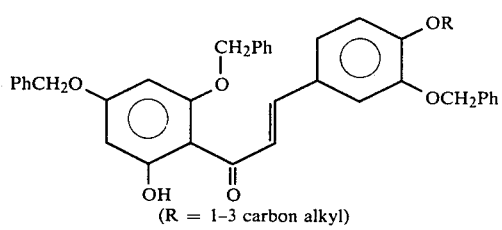

(R = 1–3 carbon alkyl)

A 500-ml, 3-neck flask, equipped with overhead stirrer, is charged with 9.04 g (25.9 mmol) of 2-hydroxy-4,6-dibenzyloxyacetophenone, 1.25 equiv. (32.4 mmol) of 4-alkoxy-3-benzyloxybenzaldehyde, and 300 ml of absolute ethanol. The mixture is stirred until a homogeneous solution is obtained, at which point 26.4 g (0.39 mol) of powdered sodium ethoxide is added. The reaction is stirred at room temperature under argon for 72 hours and then quenched by the addition of 39 g (0.65 mol) of glacial acetic acid.

The reaction mixture is evaporated to complete dryness and triturated for 30 minutes with 500 ml of boiling tetrahydrofuran and filtered. The trituration is repeated twice, and the combined filtrates are evaporated to dryness. Recrystallization from boiling toluene affords chalcone (40–65%) as a bright yellow crystalline solid. The identity and homogeneity of the product are determined by silica gel TLC (ethyl acetate-hexane, 1:1), proton NMR, and elemental analysis.

E. Preparation of 3',5,7-Trihydroxy-4'-alkoxyflavanone

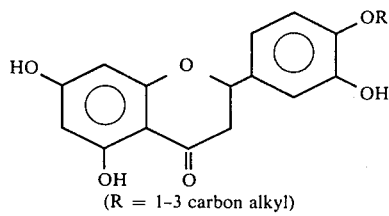

(R = 1–3 carbon alkyl)

A 1.0 mmol sample of 2-hydroxy-3',4,6-tribenzyloxy-4'-alkoxychalcone is dissolved in 40 ml of glacial acetic acid at 60° C. and treated with 2 ml of 48% aqueous HBr. The yellow solution becomes deep reddish-orange upon addition of the acid. After stirring 24 hours at this temperature, the reaction is poured into $H_2O$ (200 ml) and the resulting aqueous mixture extracted with an equal volume of ethyl acetate. The organic extract is washed with $H_2O$ (2×100 ml), 5% aqueous $NaHCO_3$ solution (2×100 ml), $H_2O$ (1×100 ml), saturated aqueous NaCl solution (1×50 ml), and dried over $MgSO_4$. Evaporation affords the crude flavanone admixed with three equivalents of benzyl bromide.

Silica gel column chromatography (elution with ethyl acetate-hexane, 1:1) affords flavanone (30–60%) as an off-white crystalline solid, which may be further purified by recrystallization. Product identity and homogeneity are determined by silica gel TLC (ethyl acetate-hexane, 1:1), proton NMR, and elemental analysis.

F. The coupling, exemplified by parts D and E, is repeated four more times varying the aldehyde among the three materials of Part A of this prepartion and the two acetophenones of Part B so, with the materials of D and E, as to yield the six possible flavanones of General Formula II which can result when X is H or OH R is $CH_3$, $C_2H_5$ or $C_3H_7$. The X equals OH, R equals $CH_3$ Flavanone, hesperetin is available commercially, as well.

EXAMPLE I

Preparation of the Aminoethyl Dihydrochalcone (IA)

(IA)

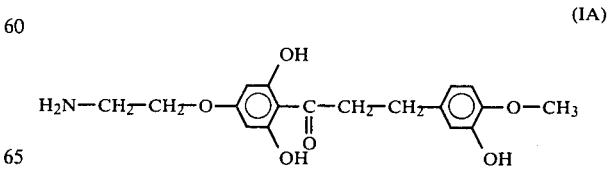

A. The flavanone hesperetin (6.04 g, 20.0 mmoles), NCBA (5.89 g, 22.0 mmols) and 22 mmoles of potassium carbonate were stirred under argon at 23° for 24 hours, then the mixture was heated to 30° and 40° C. for an additional 24 hours. Eight mmoles of NCBA were added and the mixture was held at 40° C. for 16-18 hours. The reaction was halted, the product added to 500 mls of 2% hydrochloric acid and extracted thrice with 100 ml portions of ethyl acetate. The extracts were combined, washed with water 6X and brine, dried and concentrated to give the N-carbobenzyloxyaminoethyl dihydrochalcone (IB). This material was purified by column chromatography (silica gelchloroform:methanol 99:1 eluent), followed by crystallization from hexane-ethylacetate. This material had a 129°–131° melting point.

IR: $\lambda_{max}^{KBR}$ 3.19 (O—H), 3.57, 5.92 (C=O), 6.12 (O—H), 6.63, 6.94, 7.31, 7.83, 8.28, 8.54, 9.11, 9.28, 9.70, 12.20, 13.40μ.

UV: $\lambda_{max}^{EtOH}$ 286 nm (ε=21,500).

NMR: $\delta_{acetone}^{TMS}$ 2.73–3.01 (2H multiplet, Ar—CO—CH$_2$—), 3.41–3.70 (2H multiplet, Ar—O—C—CH$_2$—N—), 3.86 (3H singlet, O—CH$_3$), 4.14 (2H triplet, J=6 Hz, Ar—O—CH$_2$—), 5.07 (2H singlet, benzyl CH$_2$), 5.43 (AB quartet, J=11 Hz, J=3 Hz, Ar—CO—C—CH—), 6.04 (2H singlet, Ar aromatic H), 6.94–7.11 (3H multiplet, Ar' aromatic H), 7.31 (5H singlet, benzyl aromatic H), 7.64 (1H singlet, N—H).

C,H Analysis: Calculated for $C_{26}H_{25}NO_8$:C, 65.13; H, 5.26 Found: C, 64.23; H, 5.30.

B. Material IB (10.1 mmoles) was dissoved in 200 mls of 10% KOH. After flushing with argon, 2.0 g 5% Pd-C was added and the reaction mixture placed in the Parr hydrogenator. After 12 hours at 26 psi, reaction was halted, and the reaction mixture was filtered through Celite and acidified to pH 5.5 by addition of 10% HC1. The turbid mixture thus obtained was then concentrated to dryness at reduced pressure yielding a mixture of white salt (KC1) and a tan solid. Fifty mls of water were added and the resulting mixture heated to 80°–90° C. for 30 minutes to dissolve salt and as much of the product as possible; most of the tan solid remained out of solution. After cooling to room temperature, filtration yielded a thick filter cake of tan solid product which was washed (2×25 ml) with ice cold H$_2$O. The mother liquor was concentrated to approximately 50 mls, whereupon a second crop of solid precipitate formed which was filtered, washed with ice cold water and combined with the first crop. The product was then dissolved with heating in approximately 150 mls H$_2$O; small amounts of insoluble material were removed by filtration through Celite. After cooling to 5°, a large amount of very fine tiny tan crystals of material IA formed. After filtering and air drying overnight, this first crop weighed 2.81 g. By HPLC analysis, this material was 99.8% pure IA. After drying in vacuo over P$_2$O$_5$ at 56° for 36 hours, this material showed mp 241°-5° (decomposed).

IR: $\lambda_{max}^{KBr}$ 3.15 (O—H, N—H), 3.37, 3,53, 3.60, 6.18 (C=O), 6.30, 6.63, 6.99, 8.07, 8.51, 9.16, 9.67, 11.02, 12.18, 13.03μ.

UV: $\lambda_{max}^{H2O}$ 285 nm (ε=20,100)

NMR: $\delta_{DMSO}^{TMS}$ 2.53–3.50 (10H multiplet, Ar—COCH$_2$CH$_2$Ar—), Ar—O—C—CH$_2$—N, O—H, NH$_3$), 3.72 (3H singlet, O—CH$_3$), 4.17 (2H triplet, J=5 Hz, Ar—O—CH$_2$—), 6.07 (2H singlet, Ar aromatic H), 6.60-6.91 (3H multiplet, Ar' aromatic H).

EXAMPLE II

Preparation of N-(2,3',6-trihydroxy-b 4'-methoxydihydrochalcone-4-ethoxy)-sulfamic acid, potassium salt.

A. Material IA, 991 mg (2.85 mmol), was reacted with 541 mg (3.14 mmol) of catechol sulfate in 15 ml DMF in the presence of 318 mg (3.14 mmol) triethylamine at room temperature for three hours. Recrystallization of the crude product IIA, N-(2,3', 6-trihydroxy-4'-methoxydihydrochalcone-4-ethoxy)-O-(2-hydroxyphenyl) sulfamate, from chloroform yielded 1.14 g (77%) of light tan granular crystals having mp 78°-80° C. TLC (chloroform-methanol; 95:5) showed one component having R$_f$=0.11. IR (KBr) 2.93 (O—H, N—H), 3.42, 3.50, 6.17 (C=O), 6.33, 6.63, 6.70, 7.01, 7.35, 8.00, 8.35, 8.54, 8.65, 9.25, 9.74, 10.41, 11.37, 12.23, 12.42, 13.16, 14.22μ; NMR (acetone d$_6$) 2.86 (t, J-7 Hz, 2H, Ar'—CH$_2$), 3.36 (t, J=7 Hz, 2H, Ar COCH$_2$), 3.63 (t, J=6 Hz, 2H, N—CH$_2$), 3.82 (s, 3H, O—CH$_3$), 4.14 (t, J=6 Hz, 2H, N—C—CH$_2$—O), 5.97 (s, 2H, ArCO aromatic H), 6.64-7.50 (m, 7H, aromatic H, aromatic H); UV (EtOH) $\lambda_{max}$ 283 (ε=21,900).

B. Twenty mmol of potassium hydroxide was added to 5.20 g (10.0 mmol) of compound IIA in a one-necked flask equipped with a stirring bar. Eighty ml of distilled water was added and the apparatus was purged with argon. The reaction mixture was refluxed for 60 minutes. Hydrochloric acid was added to pH 5-6 and the mixture concentrated to dryness at reduced pressure. The solid obtained was extracted with ether and dried to yield 4.66 g of light tan solid N-(2,3', 6-trihydroxy-4'-methoxy-dihydrochalcone-4-ethoxy)-sulfamic acid, potassium salt (IIB). HPLC (10–100% MeOH in 0.03 M KH$_2$PO$_4$ linear gradient; 15 min program; 2.0 ml/min; 286 nm) showed the desired product (RT=12.0 min) contaminated by 7% of an unknown impurity (RT=13.5 min). Comparison with a standard solution of authentic material indicated a yield of 4.23 g (91%). Recrystallization from distilled water yielded 2.79 g (60%) of tiny, white, granular crystals. IR (KBr) 2.95 (O—H), 3.30 (N—H), 3.40, 3.52, 6.17 (C=O), 6.25, 6.60, 7.00, 7.71, 8.10, 8.53, 8.89, 9.21, 9.63, 10.61, 12.13, 12.40, 13.17; NMR (DMSO d$_6$) 2.97 (t, J=6 Hz, 2H, Ar—CH$_2$), 3.16 (t, J=6 Hz, 2H, Ar—COCH$_2$), 3.30 (m, 4H, O—H, N—H, Ar'CH$_2$), 3.54 (t, J=5 Hz, 2H, N—CH$_2$), 3.70 (s, 3H, O—CH$_3$), 4.03 (t, J=5 Hz, 2H, N—C—CH$_2$—O), 5.96 (s, 2H, Ar aromatic H), 6.60-6.84 (m, 3H, Ar' aromatic H); UV (H$_2$O) $\lambda_{max}$ 282 nm (ε=20,000).

EXAMPLES III-VII

4-Aminoethoxydihydrochalcones wherein X=H and R=C$_2$H$_5$ or C$_3$H$_7$

The preparation of Example I is repeated five times with the following variation -in place of hesperetin, as a starting material, the five other flavanone starting materials prepared above are serially employed as shown in Table I.

TABLE I

| Example | X | R |
|---|---|---|
| III | OH | C$_2$H$_5$ |
| IV | OH | C$_3$H$_7$ |
| V | H | CH$_3$ |
| VI | H | C$_2$H$_5$ |
| VII | H | C$_3$H$_7$ |

This yields the five corresponding aminoethoxydihydrochalcones.

EXAMPLES VIII-XII

The five aminoethoxydihydrochalcones of Examples III through VII are reacted with catechol sulfate and processed as shown in the method of Example II. This produces the following materials.

TABLE II

SO$_3^-$K$^+$
|
HN—CH$_2$—CH$_2$—O—⌬—C—CH$_2$—CH$_2$—⌬—O—R
                    ‖
                    O
         X                          OH

| Example | X  | R       |
|---------|----|---------|
| VIII    | OH | C$_2$H$_5$ |
| IX      | OH | C$_3$H$_7$ |
| X       | H  | CH$_3$  |
| XI      | H  | C$_2$H$_5$ |
| XII     | H  | C$_3$H$_7$ |

EXAMPLE XIII

It the preceding examples, the potassium salt is formed; this corresponds to the base employed during sulfamate hydrolysis (KOH). Other salts are formed by varying the base among NaOH, Ca(OH)$_2$ and the like, or by passage of a solution of sulfamo dihydrochalcone over a strong acid ion exchange resin followed by titration with the desired metal hydroxide, or often by merely adding an excess of the desired cation to a solution of dihydrochalcone and precipitating the desired salt. In a typical preparation, a solution of the potassium salt formed in Example II is passed over a freshly washed and regenerated bed of the acidic ion exchange resin Amberlite ® 120 (Rohm and Haas) in the acid form. This forms the free acid. The solution of free acid is separated into three parts, each of which is neutralized: the first, by the addition of one equivalent of Ca(OH)$_2$; the second, by the addition of one equivalent of NaOH; and the third by the addition of one equivalent of Mg(OH)$_2$.

EXAMPLE XIV

The products of Examples II through XIII exhibit the properties of being soluble in water and other aqueous systems and of being sweet when tasted. Accordingly, they are added to the following edibles, an unsweetened cola beverage, an unsweetened lemonade base, an orange soda containing one-half its normal amount of sugar, a diet beverage containing one-fifth its normal amount of saccharin, a cough medicin and a powder for making gelatin desserts. In each application the compounds impart a desirable sweet flavor.

The product of Example II was evaluated in water by a trained test panel and found to be 352 times as sweet as sucrose on a weight basis and to have a consumer-acceptable taste profile with 89% of its taste being sweet.

What is claimed is:

1. A sulfamo dihydrochalcone compound represented by the structural formula

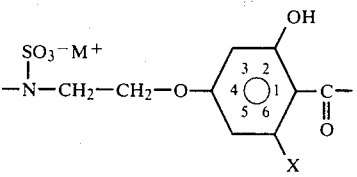
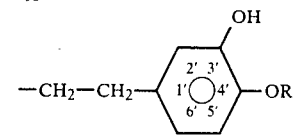

wherein R is a lower alkyl of from one to three carbon atoms inclusive, X is hydrogen or hydroxy, and M$^+$ is a physiologically acceptable cation.

2. The dihydrochalcone compound of claim 1 wherein R is methyl, X is hydrogen and M$^+$ is selected from among Na$^+$, K$^+$ and ½ Ca$^{++}$.

3. The dihydrochalcone compound of claim 1 wherein R is ethyl, X is hydrogen and M$^+$ is selected from among Na$^+$, K$^+$ and ½ Ca$^{++}$.

4. The dihydrochalcone compound of claim 1 wherein R is n-propyl, X is hydrogen and M$^+$ is selected from among Na$^+$, K$^+$ and ½ Ca$^{++}$.

5. The dihydrochalcone compound of claim 1 wherein R is methyl and X is hydroxy.

6. The dihydrochalcone compound of claim 5 wherein M$^+$ is selected from among Na$^+$, K$^+$ and ½ Ca$^{++}$.

7. The dihydrochalcone compound of claim 5 wherein M$^{30}$ is K$^+$.

8. The dihydrochalcone compound of claim 1 wherein R is ethyl, X is hydroxy, and M$^+$ is selected from among Na$^+$, K$^+$ and ½ Ca$^{++}$.

9. The dihydrochalcone compound of claim 1 wherein R is n-propyl, X is hydroxy and M$^+$ is selected from among Na$^+$, K$^+$ and ½ Ca$^{++}$.

10. A sweetened comestible material comprising an edible material having admixed therewith, as a sweetening agent, a dihydrochalcone compound of claim 1 in the amount which will afford the degree of sweetness desired.

11. A sweetened comestible material comprising an edible material having admixed therewith as a sweetening agent, the dihydrochalcone compound of claim 7 in the amount which will afford the degree of sweetness desired.

12. An amino dihydrochalcone compound represented by th structural formula

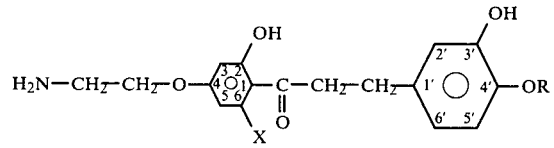

where R is a lower alkyl of from one to three carbon atoms inclusive and X is hydrogen or hydroxy.

13. The aminodihydrochalcone compound of claim 12 wherein R is methyl and X is OH.

* * * * *